United States Patent [19]

Matsumura et al.

[11] Patent Number: 4,959,483
[45] Date of Patent: Sep. 25, 1990

[54] D-GLUCOSACCHAROASCORBIC ACID

[75] Inventors: Koichi Matsumura, Ibaraki; Hiroshi Kimura, Suita; Noritoshi Mise, Takatsuki; Hiroshi Miki, Suita, all of Japan

[73] Assignee: Takeda Chemical Industries, Ltd., Osaka, Japan

[21] Appl. No.: 372,111

[22] Filed: Jun. 28, 1989

Related U.S. Application Data

[63] Continuation of Ser. No. 946,505, Dec. 19, 1986, abandoned.

[30] Foreign Application Priority Data

Dec. 25, 1985 [JP] Japan ................. 60-294575
Nov. 10, 1986 [JP] Japan ................. 61-268443

[51] Int. Cl.$^5$ ................................. C07D 307/32
[52] U.S. Cl. ........................... 549/315; 426/72
[58] Field of Search ......................... 549/315, 317

[56] References Cited

U.S. PATENT DOCUMENTS

| | | | |
|---|---|---|---|
| 2,428,438 | 10/1947 | Trenner | 549/435 |
| 2,483,251 | 9/1949 | Trenner | 549/317 |
| 2,596,103 | 5/1952 | Ruskin | 549/315 |
| 4,044,154 | 8/1977 | Hoseney et al. | 549/317 |
| 4,276,219 | 6/1981 | Andrews | 549/315 |

OTHER PUBLICATIONS

Chen, "Inorganic, Organic and Biological Chemistry" Edition. The Barnes & Noble Outline Series. p. 117.
Kasai et al., Chemical Abstracts 97 (7) 55611h w/English Translation.
Stuber et al., Carbohydrate Research, 60 (1978) 251-258.

Primary Examiner—Jane T. Fan
Attorney, Agent, or Firm—Wenderoth, Lind & Ponack

[57] ABSTRACT

Novel compounds, D-glucosaccharoascorbic acid and a salt thereof, are disclosed. The compounds, which are prepared by treating 2-keto-D-glucaric acid or an 2,3-O-acetal or ketal thereof with an acid, show excellent antioxidant activities. The agent containing the D-glucosaccharoascorbic acid or a salt thereof prevents effectively deterioration of foodstuffs.

4 Claims, 4 Drawing Sheets

Fig. 3

D-GLUCOSACCHAROASCORBIC ACID

This application is a continuation of now abandoned application Ser. No. 946,505, filed on Dec. 19, 1986.

This invention relates to D-glucosaccharoascorbic acid and salts thereof and to a method of producing the same and their use.

More particularly, the invention relates to D-glucosaccharoascorbic acid ("D-erythro-hex-2-enaro-1,4-lactone"), which is different from D-erythorbic acid in that it has a carboxyl group in place of the 6-position hydroxymethyl group of D-erythorbic acid, and salts thereof and to a method of producing the same. The compound has antioxidant activity.

This invention relates further to an agent of improving the quality of foodstuffs, the agent being prepared as containing D-glucosaccharoascorbic acid or a salt thereof, and to foodstuffs thus improved in quality.

L-Ascorbic acid, D-erythorbic acid, L-gulosaccharoascorbic acid [U.S. Pat. Nos. 2,428,438 and 2,483,251; Carbohydrate Research, 60 (1978), 251–258] and others are known to be compounds having antioxidant activity. Furthermore, L-ascorbic acid, a salt thereof, an ester derivative thereof, erythorbic acid, a salt thereof have been used as agents of improving the quality of foodstuffs.

In the course of their intensive study on the synthesis of L-ascorbic acid, D-erythorbic acid, and compounds related to them, the present inventors found that D-glucosaccharoascorbic acid, which is a novel compound, can be obtained by treating 2-keto-D-glucaric acid or an 2,3-O-acetal or ketal thereof with an acid.

Having noticed that this compound shows an excellent antioxidant activity, the present inventors have developed studies aiming at its application to foodstuffs. As a result, the present inventors found out that this compound brought about effects of improving the quality of various foodstuffs.

Based on these findings, they have now completed the present invention.

Thus, the invention provides (i) D-glucosaccharoascorbic acid and salts thereof and (ii) a method of producing D-glucosaccharoascorbic acid which comprises treating 2-keto-D-glucaric acid or an 2,3-O-acetal or ketal thereof with an acid.

The D-glucosaccharoascorbic acid of the present invention has the formula The present invention further relates to (iii) an agent of improving the quality of foodstuffs, the agent being prepared as containing D-glucosaccharoascorbic acid or a salt thereof, and (iv) to foodstuffs improved in quality by the addition of D-glucosaccharoascorbic acid or a salt thereof The D-glucosaccharoascorbic acid and its salt may be in the form of hydrate.

The compound of the invention, namely D-glucosaccharoascorbic acid, can be produced by treating 2-keto-D-glucaric acid ("D-arabino-2-hexulosaric acid") or an 2,3-O-acetal or ketal thereof with an acid. Usable as said acetal or ketal form, are those compounds whose acetal or ketal moiety is representable by the general formula wherein $R_1$ and $R_2$ are the same or different and each is a hydrogen atom, an alkyl group, or a phenyl group which may optionally be substituted, or $R_1$ and $R_2$ may combinedly form a cycloalkylene group.

The alkyl group represented by $R_1$ and/or $R_2$ is, for example, an alkyl group containing 1–5 carbon atoms, such as methyl, ethyl, propyl, i-propyl, butyl, i-butyl, sec-butyl, t-butyl, amyl or i-amyl.

When substituted, the phenyl group may have one or more substituents (e.g. 1 to 3) each selected from among a halogen atom such as fluorine, chlorine, bromine or iodine, hydroxyl, an alkoxy group containing 1–3 carbon atoms, an alkyl group containing 1–3 carbon atoms, amino, nitro, cyano, carboxyl, its $C_{1-3}$alkyl ester, carbamoyl, trifluoromethyl, and the like.

When $R_1$ and $R_2$ combinedly form a cycloalkylene group, the number of carbon atoms generally amounts to 2–6. As typical examples, there may be mentioned ethylene, trimethylene, tetramethylene, pentamethylene and hexamethylene.

As the salts of D-glucosaccharoascorbic acid, there may be mentioned an alkali metal salt (e.g. lithium salt, sodium salt, potassium salt), an alkaline earth metal salt (e.g. magnesium salt, calcium salt, barium salt) and ammonium salts. The alkali metal salt and alkaline earth metal salt are preferable, each of which may be mono- or di- salt.

The starting material for the production method may be 2-keto-D-glucaric acid or an 2,3-O-acetal or ketal, used singly, or a mixture thereof. These starting compounds may be used also in the form of a salt, such as an alkali metal salt (e.g. lithium salt, sodium salt, potassium salt), an alkaline earth metal salt (e.g. magnesium salt, calcium salt, barium salt) or an ammonium salt.

The acid to be used in the production of D-glucosaccharoascorbic acid is not limited to any particular species but includes, among others, mineral acids such as hydrogen fluoride, hydrogen chloride, hydrogen bromide, hydrogen iodide, phosphoric acid, sulfuric acid, fluorosulfuric acid and perchloric acid, and organic acids such as organic sulfonic acid (e.g. trifluoromethanesulfonic acid, methanesulfonic acid, paratoluenesulfonic acid), acetic acid, halogenated acetic acids (e.g. monochloroacetic acid, trichloroacetic acid, trifluoroacetic acid) and H+-form ion exchange resins. The acid may be used either as it is or in the form of an aqueous solution or suspension, as necessary. The acid to be used may be either a single acid or a mixture of two or more of the above-mentioned acids; any mode of use will not produce any particular difficulty.

The amount of the acid is not critical. Generally, the acid may be used from in small amounts to in large excess, namely about 0.1 to about 100 moles, preferably about 0.2 to about 50 moles, per mole of the starting material When the starting material is a salt of 2-keto-D-glucaric acid or a salt of an 2,3-O-acetal or ketal of 2-keto-D-glucaric acid, the salt-forming cation may be removed in advance by neutralization with a stoichiometric or slightly excessive amount of an acid, followed by removal of the salt formed upon neutralization by an appropriate known technique such as filtration, use of an ion exchange membrane, use of an ion exchange resin, extraction with an appropriate solvent, column chromatography or electrodialysis.

As the reaction solvent to be used in the production method, water is generally employed. However, any solvent which does not interfere with the reaction may also be used, such as aromatic hydrocarbons (e.g. benzene, toluene, xylene, chlorobenzene), halogenated or nitro aliphatic hydrocarbons (e.g. dichloromethane, chloroform, carbon tetrachloride, 1,1-dichloroethane, 1,2-dichloroethane, 1,1,2-trichloroethane, 1,1,1-trichloroethane, trichloroethylene, tetrachloroethylene, nitromethane, nitroethane), alcohols (e.g. t-butanol), ethers (e.g. ethyl ether, tetrahydrofuran, dioxane, ethylene glycol dimethyl ether, diethylene glycol dimethyl ether), ketones (e.g. acetone, methyl ethyl ketone, cyclopentanone, cyclohexanone), nitriles (e.g. acetonitrile, propionitrile or benzonitrile). The reaction may also be carried out in a mixed solvent composed of two or more of the solvents. When an organic solvent is used as the reaction solvent, the rate of reaction may be increased by adding a surfactant to the reaction system.

Examples of the surfactant are nonionic surfactants such as 18-crown-6, dibenzo-18-crown-6, [2,2,2]-cryptate and polyoxyethylene alkylaryl ether, cationic surfactants such as various ammonium salts, e.g. tetrapropylammonium chloride, benzyltrimethylammonium bromide, phenyltriethylammonium chloride, cetyltrimethylammonium chloride, stearyltrimethylammonium bromide, 1-phenacylpyridinium chloride and stearylpropylenediamine dihydrochloride, and phosphonium salts, e.g. benzyltriphenylphosphonium chloride and vinyltriphenylphosphonium bromide, and anionic surfactants such as higher fatty acids and alkylarylsulfonates. These may be used either singly or in combination of two or more without causing any particular difficulty. The surfactant is used in an amount within the range of about 0.05–5% by weight, preferably 0.1 to 3% by weight, on the starting material substrate basis.

While the reaction temperature is not critical, the reaction is generally carried out within the temperature range of about 0° C. to about 150° C., preferably within the range of about 10° C. to about 100° C.

The reaction period may vary depending on the kind of starting material, the kind of salt, the kind of acid, the quantity of acid, the reaction conditions and other factors. Generally, however, the reaction is conducted for about 10 minutes to about 24 hours, preferably for about 20 minutes to about 12 hours.

The procedure for the isolation of D-glucosaccharoascorbic acid thus produced somewhat differs depending on whether the starting material is the free acid or a salt thereof. Thus, when the starting material is a salt of 2-keto-D-glucaric acid or a salt of 2,3-O-acetal or ketal of 2-keto-D-glucaric acid and when the byproduct salt formed by the neutralization reaction with the acid has not been removed in advance during the reaction process, removal of the salt is required. The desalting procedure is performed by subjecting the reaction mixture, either as it is or after appropriate treatment such as solvent removal, to known desalting treatment, such as filtration, ion exchange membrane treatment, ion exchange resin treatment, extraction with an appropriate solvent, column chromatography, electrodialysis, or an appropriate combination thereof.

Where the starting material is 2-keto-D-glucaric acid or an 2,3-O-acetal or ketal of 2-keto-D-glucaric acid, or where though the starting material is a salt of 2-keto-D-glucaric acid or a salt of 2,3-O-acetal or ketal of 2-keto-D-glucaric acid, its desalting procedure has been performed during the reaction process, the desired D-glucosaccharoascorbic acid can be readily isolated and purified by known techniques, for example by removing the solvent and low-boiling substances from the reaction mixture by a conventional method and subjecting the residue to extraction, column chromatography, recrystallization and/or the like. In this case, D-glucosaccharoascorbic acid may be isolated as its free form or in the form of hydrate.

For the isolation of D-glucosaccharoascorbic acid in a salt form, D-glucosaccharoascorbic acid or its hydrate can be converted to the salt form by reacting with an appropriate base, such as an alkali metal oxide, an alkali metal hydroxide, an alkali metal carbonate or bicarbonate, an alkaline earth metal oxide, an alkaline earth metal hydroxide, an alkaline earth metal carbonate or an appropriate amine or by contacting with a cation exchange resin substituted by an appropriate alkali metal or alkaline earth metal or an appropriate ammonium. It is also possible to neutralize the reaction mixture, without isolating D-glucosaccharoascorbic acid, with an appropriate base, such as an alkali metal oxide, an alkali metal hydroxide, an alkali metal carbonate or bicarbonate, an alkaline earth metal oxide, an alkaline earth metal hydroxide, an alkaline earth metal carbonate or an appropriate amine or bring the reaction mixture into contact with a cation exchange resin substituted by an appropriate alkali metal or alkaline earth metal or an appropriate ammonium, to thereby convert the product directly to a salt of D-glucosaccharoascorbic acid or its hydrate and then isolate and purify the desired salt of D-glucosaccharoascorbic acid or its hydrate by known means or methods, for example solvent removal followed by recrystallization or reprecipitation.

2-Keto-D-glucaric acid or a salt thereof to be used as the starting material in the production method is producible in the following manner. Among usable starting compounds, the calcium salt of 2-keto-D-glucaric acid is a known compound synthesizable by subjecting D-glucaric acid to oxidation using a microorganism belonging to the genus Pseudomonas [Czechoslovakian Patent No. 222,577 (1984); Chemical Abstracts, vol. 101, 22036x]. 2-Keto-D-glucaric acid can also be synthesized by subjecting D-glucose to one-step fermentative oxidation using a strain of the genus Pseudogluconobacter [e.g. *Pseudogluconobacter saccharoketogenes* K591S (FERM P-8481, IFO 14464)] and can be isolated easily in the form of calcium salt which is sparingly soluble in water. The calcium salt of 2-keto-D-glucaric acid can be converted to free 2-keto- D-glucaric acid by treating with an acid or a cation exchange resin ($H^+$ form) while the free acid can be converted to a salt of 2-keto-D-glucaric acid by a conventional method.

The 2,3-O-acetal or ketal of 2-keto-D-glucaric acid can be produced by acetalizing or ketalizing 2-keto-D-glucaric acid. The acetalization or ketalization is carried out by bringing 2-keto-D-glucaric acid or a salt thereof into contact with an aldehyde or ketone or a reactive derivative thereof in the presence of an appropriate acetalization or ketalization catalyst As the above-mentioned aldehyde or ketone, a compound of the general formula $R_1COR_2$ ($R_1$ and $R_2$ being as defined above) is used.

As the reactive aldehyde or ketone derivative, there may be mentioned compounds of the general formula wherein $R_1$ and $R_2$ are as defined above and $R_3$ and $R_4$ are the same or different and each is an alkyl group containing 1-5 carbon atoms or $R_3$ and $R_4$ combinedly form a cycloalkyl group containing 2-6 carbon atoms. Examples of $R_3$ and $R_4$ are methyl, ethyl, propyl, i-propyl, n-butyl, i-butyl, sec-butyl, t-butyl, amyl, i-amyl and, when $R_3$ and $R_4$ are combined, ethylene, trimethylene, tetramethylene, pentamethylene and hexamethylene.

The acetalization or ketalization reaction can be carried out, for example by the method shown later herein in some reference examples using a known acid catalyst (Japanese Kokai Tokkyo Koho No. 60-72895).

The agent of this invention can contain D-glucosaccharoarscorbic acid, a salt thereof or a hydrate of said acid or salt and an edible carrier therefor, such as a solvent (e.g. water, ethanol, etc.), an emulsifier (e.g. glycerin fatty acid ester, sucrose fatty acid ester, propylene glycol fatty acid ester, etc.), a thickening agent, a stabilizing agent, and, further, burnt alum, wheat flour or calcium carbonate. The agent of the present invention can also be used in combination with a variety of food additives (e.g. condiments, an acidulant, a sweetening agent, coloring agent, a flavoring agent, a preserving agent, a germicide or an antioxidant).

Foodstuffs which can be the subjects whose quality is to be improved are animal foods and vegetable foods or processed products thereof. More concretely, they are exemplified by oils and fats, foods containing oils and fats, meat or meat products, fruits or fruit products, vegetable or vegetable products, milk or dairy products, soybean paste, soy sauce, and, further, beverage such as beer, wine etc.

The agent of this invention shows an antioxidant activity against oils and fats or foods containing oils and fats, and the oils and fats and the foods containing oils and fats incorporated with the agent are prevented from deterioration due to oxidation. These oils and fats are exemplified by unsaturated fatty acids such as oleic acid, linoleic acid or linolenic acid; natural fats and oils such as cotton seed oil, safflower oil, coconut oil, corn oil, soybean oil, sesame oil, olive oil, peanut oil, palm oil, beef tallow, lard, fish oil or whale oil; or food products containing any of them. In case of aiming at preventing oils and fats from oxidation, the amount of the agent ranges usually from 0.01 weight % to 1.0 weight %, preferably 0.02-0.5 weight % calculated as the amount of D-glucosaccharoascorbic acid or salt thereof, and, practically it may be suitably selected depending on the subject food products. The present inventors further found out that D-glucosaccharoasoorbic acid when used in combination with tocopherol which has been known as an antioxidant of food products can be a more excellent antioxidant. The tocopherol to be used can be exemplified by α-tocopherol, β-tocopherol, γ-tocopherol, δ-tocopherol or a mixture thereof (e.g. natural tocopherol obtainable from vegetable oil, germ, etc.). The amount of tocopherol to be used is that which is conventionally used as an additive to food products as an antioxidant, for example, 0.005-1.0 weight %, preferably 0.01-1.0 weight %.

Another subject to which the agent of this invention can be applied is exemplified by meat or meat products.

The agent of this invention is effective in preventing discoloration of meat. The meat to which the agent of this invention is added is kept from browning and retains its scarlet color. The agent of this invention is also effective in promoting color-development and preventing discoloration, and in accelerating the action of a colorant such as nitrate, nitrite, etc., while preventing thus-produced color from fading. The meat is exemplified by beef, pork, mutton, chicken or minced meat thereof as well as fresh fishery products. The meat products, which are prepared from such meat as set forth above, are exemplified by ham, sausage, bacon, hamburger, roast pork, dried fish, smoked products salted food, canned products, fish paste products, etc. The agent of this invention has also an activity of suppressing the production of nitrosoamine, which is known as having problematic issue in safety, in meat products, and an activity of suppressing the production of trimethylamine emitting a putrid smell in fishery products. The amount of the agent of this invention, when added to meat or meat products, and the manner of the addition can be selected suitably depending on the food products to which the agent is to be added. Usually, the agent of this invention is added within the range of 0.01-1.0 weight %, preferably 0.02-0.5 weight % calculated as the amount of D-glucosaccharoascorbic acid or salt thereof directly to a food product or its 0.01-1.0 %, preferably, 0.02-0.5 % aqueous solution is sprayed on a food, or, depending on the case, food products may be immersed in this aqueous solution.

The agent of this invention can be used also for improving dairy products in quality.

The agent of this invention is effective in preventing milk or dairy products from emission of unpleasant smell and in preventing them from deterioration. The milk or dairy products, to which the agent of this invention is added, are prevented from emission,- of oxidized smell, beef tallow smell, taint odor and skunky smell during the period of storage, and also are prevented from decomposition of vitamin A contained therein. Milk or dairy products are exemplified by fresh milk, fresh goat's milk, cow's milk, special milk, sterilized goat's milk, skim milk, processed milk, cream, concentrated milk, evaporated milk, sweetened condensed milk, sweetened evaporated dry milk, skim milk powder, sweetened dry milk, milk beverage, fermented milk, lactic acid beverage, butter, cheese, ice-cream, ice-milk, lacto-ice, food products whose principal material is milk or the like, etc. The amount of the agent of this invention, when added to milk or dairy products, and the manner of the addition can be selected suitably depending on the food products to which the agent is to be added. Usually, the agent of this invention is added, in the course of preparation, within the range of 0.01-1.0 weight %, preferably 0.01-0.5 weight % calculated as the amount of D-glucosaccharoaoscorbic acid or salt thereof.

The agent of this invention can further be used for improving fruits, vegetables and their processed products.

The agent of this invention shows an action of preventing fruits and their processed products from discoloration, color-fading and flavor-deterioration. These fruits and their processed products are exemplified by apple, peach, banana, apricot, pear, plum as well as frozen products thereof, chilled products thereof, beverages, canned products, dried fruits.

The amount of the agent of this invention to be added and the manner of the addition can be selected suitably depending on the subject food products. Usually, in the course of manufacturing, the agent of this invention is directly added to such products in an amount ranging from 0.01 weight % to 1.0 weight % calculated as the amount of D-glucosaccharoascorbic acid or salt thereof, or is sprayed on food products as a 0.01–1.0% aqueous solution, or such food products may be immersed into the aqueous solution.

The present inventors further found out that the use of D-glucosaccharoascorbic acid in combination with table salt or(and) citric acid or(and) malic acid brought more excellent effects in preventing food products from discoloration, color-fading and flavor-deterioration. The respective weight ratios of table salt, citric acid and malic acid to one part by weight of D-glucosaccharoascorbic acid are 0.1–50, preferably 0.1–20; 0.1–100, preferably 0.2–50; and 0.1–100, preferably 0.2–50. Practically, the ratio may be suitably selected depending on the subject food products.

The agent of this invention is also effective in preventing vegetables and processed products thereof from discoloration, color-fading and flavor-deterioration. Vegetables and processed products thereof are exemplified by burdock roots, butterburs, Japanese eggplants, potatoes, radishes, yams, mushrooms, sweet potatoes, cauliflowers, cabbages, lettuce, carrots; frozen products, chilled products, beverages and canned products processed from those vegetables. The amount and manner of adding the agent of this invention to those vegetables and processed vegetable products are the same as those in the case of fruits and fruit processed products, which can be suitably selected depending on the subject food products.

The agent of this invention can also be used for improving quality of beverages.

The agent of this invention also serves to prevent beer or wine from deterioration such as appearance of clouds, formation of precipitates, discoloration and flavor-deterioration. The amount of the agent of this invention to be used is 5–100 mg, preferably 10–70 mg calculated as D-glucosaccharoascorbic acid or salt thereof relative to 1l of beer or wine, and the agent may be added in the course of manufacture of beer or wine.

The quality-improving agent of this invention prevents effectively deterioration of foodstuffs due to e.g. oxidation, performing excellent effects for maintaining and improving quality of foodstuffs.

The following reference examples and working examples are further illustrative of the present invention.

REFERENCE EXAMPLE 1

A medium (PYG medium, 30 ml) containing 0.5% of peptone, 0.5% of yeast extract, 1.0% of glucose and 0.1% of K was placed in a 200-ml Erlenmeyer flask and steam-sterilized at 120° C. for 20 minutes. This flask was inoculated with one loopful of fresh cells of *Pseudomonas aeruginosa* IFO 3448 grown at 28° C. for 2 days on a slant medium prepared by supplementing PYG medium with 2.0% of agar. Cultivation was conducted at 30° C for 24 hours with rotation for shaking (200 rpm) to give a seed culture.

After preliminary pH adjustment to 7.0 with NaOH and bacterial filtration using a 0.45-micron filter, monopotassium D-glucarate (Sigma) was added to PYG medium to a concentration of 1%. To a 200-ml Erlenmeyer flask containing 20 ml of this medium was transferred 1 ml of the above seed culture, and shake culture was performed at 30° C. for 24 hours. High performance liquid chromatography [high performance liquid chromatography using a sulfonated polystyrene gel-packed column (Shimadzu SCR-101H column, 7.9 mm × 30 cm) (mobile phase: diluted sulfuric acid, pH 2.2; flow rate: 0.5 ml/min.; detector: differential diffractometer)] revealed that thus-obtained culture broth contained 9.02 mg/ml of 2-keto-D-glucaric acid. Cells were removed from 590 ml of such culture broth by centrifugation to give 580 ml of a supernatant. The supernatant was deprived of the cation by passing through an Amberlite cation exchange resin IR120 (H+ form, 200 ml) column and washing the column with 150 ml of deionized water and then decolorized by passing through an active carbon (70 ml) column and washing the column with 50 ml of deionized water. The effluent (780 ml) was adjusted to pH 6.5 with Ca(OH)$_2$, filtered to remove turbidity and then concentrated to about 20 ml under reduced pressure. White amorphous crystals formed in the concentrate. The crystals were collected on a glass filter, washed with small amounts of cold water, methanol and ethyl ether, and dried under reduced pressure to give 5.04 g of 2-keto-D-glucaric acid 3.5 hydrate. The analytical data for the crystals were as shown below.

Melting point: 152°–157° C. (decomposition).

Elemental analysis (%): For $C_6H_6O_8 \cdot Ca \cdot 3.5H_2O$. Calculated: C, 23.30; H, 4.24; Ca, 12.96. Found C, 23.15; H, 4.18; Ca, 14.00.

Specific rotation: $[\alpha]_D^{25} = -11.0°$ (c=1.075%, 0.1 HCl, immediately after dissolution). $[\alpha]_D^{25} = +9.0°$ (c=1.075%, 0.1 N HCl, after equilibration).

Infrared absorption spectrum (IR):

The wave numbers (cm$^{-1}$) of main absorption maxima as determined by the KBr method are as follows: 3590, 3500, 3400–2700 (br), 1650, 1600, 1430, 1380, 1360, 1300, 1250, 1240, 1220, 1125, 1095, 1065, 1040, 1005, 995, 955, 900, 840, 800, 765,

REFERENCE EXAMPLE 2

A seed culture medium (20 ml) containing 2.0% of D-glucose, 1.0% of peptone, 1.0% of dried yeast and 2.0% of CaCO$_3$ was placed in a 200-ml Erlenmeyer flask and steam-sterilized in advance at 120° C. for 20 minutes. One loopful of cells of *Pseudogluconobacter saccharoketogenes* K591S (FERM P-8481, IFO 14464) grown at 28° C. for 4 days on a slant medium containing 2.5% of D-sorbitol, 1.0% of peptone, 1.0% of yeast extract, 0.2% of CaCO$_3$ and 2.0% of agar was inoculated into the flask and shake culture (200 rpm) was performed at 30° C. for 2 days to give a seed culture broth. The same medium as the seed culture medium was distributed in 200-ml portions into one-liter Erlenmeyer flasks and sterilized in the same manner as mentioned above. After inoculation of 10 ml of the seed culture broth into each flask, shake culture was performed at 30° C. for 3 days.

The culture broth thus obtained was found to contain 19.4 mg/ml of 2-keto-D-glucaric acid.

The culture broth (1,600 ml) was centrifuged (7,000 rpm, 10 minutes) to remove the cell-containing precipitate. The thus-obtained supernatant (1,520 ml) was cooled to 4° C. and allowed to stand for 3 days, whereupon amorphous crystals of dicalcium 2-keto-D-glucarate precipitated out. The crystals were collected on a glass filter (No. 3), washed with small amounts of water, methanol and ethyl ether and dried over phosphorus pentoxide under reduced pressure. Thus was obtained 18 g of dicalcium 2-keto-D-glucarate trihydrate. The analytical data for the crystals obtained were as shown below.

Melting point: 152°–157° C. (decomposition).

Elemental analysis (%): For $C_6H_6O_8 \cdot Ca \cdot 3H_2O$ Calculated: C, 24.00; H, 4.03; Ca, 13.35. Found: C, 23.96; H, 4.16; Ca, 13.00. Specific rotation: $[\alpha]_D^{25} = -12.3°$ (c=1.065%, 0.1 NHCl, immediately after dissolution). $[\alpha]_D^{25} = +7.9°$ (c=1.065%, 0.1 NHCl, after equilibration).

These crystals showed the same infrared spectrum as that of the crystals obtained in Reference Example 1. The retention time (9.4 minutes) in high performance liquid chromatography and the intensity ratio (about 1.0) between the ultraviolet absorption at 214 nm and differential diffraction were the same as those for the crystals obtained in Reference Example 1. The sample of the product obtained in this reference example and that of the product obtained in Reference Example 1 both showed an $R_f$ value of 0.20 in thin layer chromatography after 3 hours of development at room temperature on a cellulose plate (Merck) with the solvent system phenolformic acid-water (75:5:25). Both the samples showed the same color reactions: they developed a dark brown color against the silver nitrate reagent, a yellow color against the o-phenylenediamine reagent and a yellow color against the aniline-phthalic acid reagent.

Based on the above analytical results, the glucose metabolite produced by *Pseudogluconobacter saccharoketogenes* K591S was identified as 2-keto-D-glucaric acid.

REFERENCE EXAMPLE 3

Five grams of crude dicalcium 2-keto-D-glucarate [the content of dicalcium 2-keto-D-glucarate trihydrate ($C_6H_6O_8 \cdot Ca \cdot 3H_2O$) as determined by high performance liquid chromatography (see Note below) being 85.1%] obtained in the same manner as in Reference Example 2 was placed in a 500-ml Erlenmeyer flask, 300 ml of distilled water was added thereto and the mixture was stirred to give a suspension. To the suspension was added 60 ml of the cation exchange resin IR-120B (Rohm and Haas, U.S.A.) ($H^+$ form) The mixture was stirred at room temperature for 1 hour. The reaction mixture was filtered through a glass filter, and the solid matter on the filter was washed with 100 ml of distilled water. The filtrate and the washings were combined and concentrated to about 50 ml under reduced pressure. The concentrate was finely filtered through a Millipore filter paper (GSWPO 4700, Millipore, U.S.A., pore size 0.22 um) covered with about 10 g of Hyflo Super Cel (Celite of Johns-Manville, U.S.A.). The filter was washed with 20 ml of distilled water. The filtrate and the washings were combined. High performance liquid chromatography revealed that they contained 2.66 g of 2-keto-D-glucaric acid (90.1% recovery). The combined filtrate was passed through a column packed with 10 g of active carbon (Shirasagi®A for chromatography, Takeda Chemical Industries). The column was washed with 100 ml of distilled water. The combined effluent was distributed in two equal portions into two 500-ml eggplant-shaped flask and the water was removed by lyophilization. Seven hours later, the colorless oil obtained was dried over phosphorus pentoxide under reduced pressure for 3 hours and submitted to elemental analysis and IR spectrometry.

Elemental analysis (%): For $C_6H_8O_8 \cdot 1.4H_2O$ Calculated: C, 30.88; H, 4.66. Found: C, 31.12; H, 4.57.

High performance liquid chromatography (see Note below):

Retention time: 7.30 min. IR (film), $cm^{-1}$: 3700–2700, 1730, 1700 sh, 1680 sh, 1640.

Note:

High performance liquid chromatography conditions:
  HPLC: Shimadzu model LC-3A
  Column: Aminex ion exclusion HPX-87H, 300×7.8 mm (Bio-Rad)
  Flow rate: 0.6 ml/min
  Column temperature: 25° C.
  Mobile phase: 0.008 N $H_2SO_4$
  Detector: UV (210 nm) and RI (Showa Denko model SE-31)

REFERENCE EXAMPLE 4

Crude dicalcium 2-keto-D-glucarate (100 g) [the content of dicalcium 2-keto-D-glucarate trihydrate ($C_6H_6O_8 \cdot Ca \cdot 3H_2O$) as determined by high performance liquid chromatography under the same conditions as used in Reference Example 3 being 85.1%]obtained in the same manner as in Reference Example 2 was placed in a 2-liter beaker and 500 ml of distilled water was added thereto. The mixture was stirred until it became a suspension (the pH being 8.27 then). About 1 liter of the cation exchange resin IR-120B ($H^+$-form) (Rohm and Haas, U.S.A.) was added gradually to the suspension with stirring. After completion of the addition, stirring was further continued for 1 hour, whereupon the pH of the reaction mixture became 1.36 and thereafter remained constant. The reaction mixture was filtered through a glass filter, and the solid matter was washed with distilled water (about 400 ml×4). The filtrate (730 ml) and the washings (1,740 ml) were individually assayed by liquid chromatography. It was found that the filtrate contained 48.7 g and the washings 9.1 g of 2-keto-D-glucaric acid. The total amounted to 57.8 g, hence the free acid recovery was 97.9%. The filtrate and the washings were combined and concentrated to about 300 ml under reduced pressure. Active carbon (1 g) was added to the concentrate and the mixture, after stirring, was finely filtered through a Millipore filter paper (GSWPO 4700, Millipore, U.S.A., pore size 0.22 μm) covered with about 20 g of Hyflo Super Cel (Celite of Johns-Manville, U.S.A.). The filter was washed with distilled water (50 ml×2) and the washings were combined with the filtrate. High performance liquid chromatography showed that the combined filtrate contained 52.3 g of 2-keto-D-glucaric acid, hence the recovery was 88.6%. This was concentrated under reduced pressure to give 62.5 g of a pale yellow syrup. The content of 2-keto-D-glucaric acid was 83.7%. (Yield 88.7%)

REFERENCE EXAMPLE 5

An aqueous solution (10 ml) containing 2.71 g (0.013 mole) of 2-keto-D-glucaric acid was diluted to 30 ml with distilled water and, with stirring, 0.96 g (0.013 mole) of calcium hydroxide was added. After stirring at room temperature for 2 hours, the insoluble matter was collected by filtration, washed with about 200 ml of water and dried in a desiccator under reduced pressure to give 3.84 g of dicalcium 2-keto-D-glucarate. (Yield 98.4%)

Melting point: about 155° C (decomposition).

Elemental analysis (%): For $C_6H_6O_8Ca\cdot 3H_2O$ Calculated: C, 24.00; H, 4.03. Found: C, 23.94; H, 3.99.

The content of water of crystallization in this product can vary readily depending on the conditions of drying. For instance, drying at room temperature for a prolonged period of time gave 2.5 hydrate, drying at 40° C. for 6 hours gave dihydrate, and drying at 60° C. for 6 hours gave monohydrate.

IR (KBr), $cm^{-1}$: 3650–2900, 1650, 1600, 1420.

$^{13}C$ NMR ($D_2O$+DCl), δ: 182.7(s), 182.4(s), 174.6(s), 174.3(s), 172.1(s), 105.8(s), 100.6(s), 82.8(d), 81.7(s), 79.4(d), 79.1(d), 78.5(d), 77.4(d)°

REFERENCE EXAMPLE 6

A 10-ml 2-keto-D-glucaric acid solution prepared from 5.0 g of crude dicalcium 2-keto-D-glucarate (content as trihydrate, $C_6H_6O_8Ca\cdot 3H_2O$, 85.1%) by following the procedure of Reference Example 4 [said solution containing 2.71 g (0.013 mole) of 2-keto-D-glucaric acid as determined by high performance liquid chromatography; yield 92.0%]was applied to a column packed with 30 ml of Dowex 50W-X8 (cation exchange resin of Dow Chemical, USA) ($Na^{30}$ form). Elution was carried out with distilled water to give an eluate (400 ml, pH 3.4). This eluate was concentrated to dryness under reduced pressure, 400 ml of methanol was added to the residue, and the mixture was stirred, whereby the residue became a powder. This was collected by filtration, washed with a small amount of acetone and then dried in a desiccator under reduced pressure to give 2.44 g of monosodium 2-keto-D-glucarate.

(Yield 75.6%) Melting

Melting point: 155°–160° C. (decomposition).

Elemental analysis (%): For $C_6H_7O_8Na\cdot H_2O$ Calculated: C, 29.04; H, 3.66. Found: C, 28.72; H, 3.80.

IR (KBr), $cm^{-1}$: 3600–1800, 1720, 1620, 1410

REFERENCE EXAMPLE 7

A 10-ml 2-keto-D-glucaric acid solution prepared from 5.0 g of crude dicalcium 2-keto-D-glucarate (content as trihydrate, $C_6H_6O_8Ca\cdot 3H_2O$, 85.1%) by following the procedure of Reference Example 4 [said solution containing 2.71 g (0.013 mole) of 2-keto-D-glucaric acid as determined by high performance liquid chromatography] was applied to a column packed with 30 ml of Dowex 50W-X8 ($K^+$ form). Elution was carried out with distilled water to give an eluate (400 ml, pH 3.42). This eluate was concentrated under reduced pressure, 400 ml of methanol was added to the residue, and the mixture was stirred, whereupon the residue gave a powder. This was collected by filtration, washed with a small amount of acetone and then dried in a desiccator under reduced pressure to give 2.12 g of monopotassium 2-keto-D-glucarate. (Yield 61.7%)

Melting point: 135°–150° C. (decomposition).

Elemental analysis (%): For $C_6H_7O_8K\cdot H_2O$. Calculated: C, 27.27; H, 3.43. Found: C, 26.83; H, 3.66.

IR (KBr), $cm^{-1}$: 3600–2800, 1720, 1610, 1410.

REFERENCE EXAMPLE 8

To a stirred suspension of 5.0 g (0.0167 mole) of dicalcium 2-keto-D-glucarate trihydrate in 250 ml of acetone was added gradually 2.5 ml of concentrated sulfuric acid. After completion of the addition, stirring was continued for further 3 hours. The insoluble matter was then filtered off using about 20 g of Hyflo Super Cel (Johns-Manville, U.S.A.) as a filter aid, and washed with about 1,000 ml of acetone. The filtrate and the washings were combined and concentrated under reduced pressure, and the crystalline precipitate was collected by filtration, washed with a small amount of ethyl acetate and then dried in a desiccator to give 3.80 g of 2.3-O-isopropylidene -2-keto-D-glucaric acid as colorless needles. (Yield 91.7%)

Melting point: 180°–210° C. (decomposition) (recrystallized from acetone-ether)

Elemental analysis (%): For $C_9H_{12}O_8$ Calculated: C, 43.56; H, 4.87. Found: C, 43.57; H, 4.99.

IR (KBR), $cm^{-1}$: 3400, 3300–2800, 1750, 1690.

$^1H$-NMR ($d_6$-DMSO), δ: 1.30(s, 3H), 1.39(s, 3H), 4.35–4.7(m, 3H), 8–10(br, 3H).

$^{13}C$-NMR ($D_2O$), δ: 25.3(q), 25.5(q), 76.7(d), 86.7(d), 111.8(s), 116.7(s), 170.4(s), 173.0(s).

REFERENCE EXAMPLE 9

A mixture composed of 7.10 g of syrupy crude 2-keto-D-glucaric acid (the content being 83.7% as determined by high performance liquid chromatography; 0.0286 mole), 15 ml of benzaldehyde, 50 ml of acetonitrile and 2 drops of concentrated sulfuric acid was refluxed with stirring for 4.5 hours, during which 20 g of molecular sieve 3A placed between the reactor and the condenser served for drying the refluxing solvent. Analysis of the reaction mixture by high performance chromatography [conditions of analysis - column: Aminex HPX-87H (Bio-Rad); mobile phase: 0.008 N $H_2SO_4$; flow rate: 0.6 ml/min.; detector: SE-31 (Showa Denko)]showed formation of 2,3-O-benzylidene isomers in a ratio of about 60:40. The reaction mixture was concentrated under reduced pressure and ether was added to the paste-like residue, whereupon the major isomer mainly became a powder. This was collected by filtration, washed with a small amount of ether, dried and recrystallized from acetonitrile to give 3.81 g of 2,3-O-benzylidene-2-keto-D-glucaric acid. Analysis of this product by high performance liquid chromatography indicated that it was composed of a great majority of the major isomer and a small percentage of the minor isomer. (Yield 45.0%)

Melting point: 198°–199° C. (decomposition).

Elemental analysis (%): For $C_{13}H_{12}O_8$ Calculated: C, 52.71; H, 4.08. Found: C, 52.73; H, 4.02.

IR (KBr), $cm^{-1}$: 3500–3000, 1740, 1710.

$^1H$-NMR ($d_6$-DMSO), δ: 4.50 (s, 2H), 4.75(d, 1H), 6.15(s,1H), 7.43(s, 5H), the signals for OH and COOH were very broad, so that they could not be expressed numerically.

EXAMPLE 1

A mixture of 24.8 g (0.1 mole) of 2,3-O-isopropylidene-2-keto-D-glucaric acid and 50 ml of concentrated hydrochloric acid was stirred at 50° C. for 20 minutes. The reaction mixture was concentrated to dryness under reduced pressure, 10 ml of distilled water were added to the residue, and the solution was passed through the column packed with 50 ml of active carbon (Shirasagi ®; special. grade for chromatography, manufactured and sold by Takeda Chemical Co., Ltd.) with the aid of water. After being eluted with water, the elute was concentrated under reduced pressure. To the residue was added a small amount of dichloromethane, and the insoluble matter was collected by filtration and dried to give 19.0 g of crude D-glucosaccharoascorbic acid (D-erythro-hex-2-enaro-1,4-lactone).monohydrate. Purity: 98.5%; Yield: 90.0%

There was obtained pure D-glucosaccharoascorbic acid by the recrystallization from dried acetonitrile.

Melting point: 188°–189° C. (decomposition)

Elemental analysis (%): for $C_6H_6O_7$ Calculated: C, 37.91; H, 3.16. Found: C, 37.80; H, 3.21.

IR (KBr), cm$^{-1}$: 3580, 3500, 3400–3000, 1770, 1720, 1690, 1590.

$^1$H-NMR (d$_6$-DMSO), δ: 4.42(d, 1H), 4.95(d, 1H), 6.5–9.5(br, 2H), 9.5–13(br, 2H)

$^{13}$C-NMR, δ: 69.5(d, C at position 5), 77.2(d, C at position 4), 118.9(s, C at position 2), 152.3(s, C at position 3), 170.5(s, C at position 1), 171.7(s, C at position 6)

EXAMPLE 2

A mixture composed of 2.48 g (0.01 mole) of 2,3-O-isopropylidene-2-keto-D-glucaric acid and an aqueous solution of an acid given in Table 1 was stirred at 65° C. for 2 hours. After completion of the reaction period, the reaction mixture was made 100 ml and assayed by high performance liquid chromatography [column: Zorbax BP-NH$_2$, 4 mm×250 mm; mobile phase: 25% 0.01 M KH$_2$PO$_4$-75% acetonitrile; flow rate: 1.5 ml/min.; detector: SE-31 (Showa Denko)]. D-Glucosaccharoascorbic acid was obtained in the yield given in Table 1.

TABLE 1

| Acid No. | (10 ml) | D-Glucosaccharoascorbic acid g | Yield (%) |
|---|---|---|---|
| 1 | 10% HCl | 1.82 | 95.8 |
| 2 | 10% HBr | 1.73 | 91.1 |
| 3 | 10% HI | 1.76 | 92.8 |
| 4 | 10% H$_2$SO$_4$ | 1.49 | 78.6 |
| 5 | 5% HClO$_4$ | 1.70 | 89.6 |
| 6 | 10% CH$_3$SO$_3$H | 1.32 | 69.6 |
| 7 | 5% CF$_3$SO$_3$H | 1.68 | 88.6 |
| 8 | 50% CF$_3$COOH | 1.66 | 87.6 |
| 9 | 50% CH$_3$COOH | 0.99 | 52.3 |
| 10 | IR-120B (H$^+$form) 4 ml-H$_2$O (20 ml in total) | 1.79 | 94.4 |

EXAMPLE 3

A mixture of 3.06 g (0.01 mole) of 2,3-0-cyclo-hexylidene-2-keto-D-glucaric acid and 6 ml of concentrated hydrochloric acid was stirred at 70° C. for 30 minutes. The reaction mixture was concentrated to dryness under reduced pressure, a small amount of active carbon and 50 ml of distilled water were added to the residue, and the mixture was heated for about 5 minutes and filtered while hot. The filtrate was concentrated to dryness under reduced pressure, a small amount of dichloromethane was added to the residue, and the insoluble matter was collected by filtration and dried to give 1.69 g of D-glucosaccharoascorbic acid·monohydrate (Purity 98.0%). (Yield 79.6%)

EXAMPLE 4

2,3-0-Benzylidene-2-keto-D-glucaric acid (1.48 g, 0.005 mole) was dissolved in 10 ml of 20% hydrochloric acid and the solution was stirred at 70° C. for 1 hour. Thereafter, the total amount was made 100 ml and assayed by high performance liquid chromatography, which indicated formation of 0.82 g of D-glucosaccharoascorbic acid. (Yield 85.8%)

EXAMPLE 5

A mixture composed of 24.9 g of syrupy crude 2-keto-D-glucaric acid (having a purity of 83.7% as determined by high performance liquid chromatography; 0.10 mole), 15 ml of concentrated hydrochloric acid and 150 ml of toluene was stirred at 65° C. (reactor inside temperature) for 4 hours. Thereafter, the reaction mixture was concentrated to dryness, 1.0 g of active carbon and 200 ml of water were added, and the mixture was heated for about 5 minutes and then filtered using a glass filter. The filtrate was assayed in the conventional manner by high performance liquid chromatography, which showed formation of 17.7 g of D-glucosaccharoascorbic acid. (Yield 93.3%)

The filtrate was again concentrated to dryness under reduced pressure, a small amount of ether was added to the residue, and the insoluble matter was collected by filtration, washed with a small amount of dichloromethane, dried and recrystallized from an acetone-benzene mixture to give 15.8 g of D-glucosaccharoascorbic acid. (Yield 83.1%) Melting point: 188°–189° C. (decomposition)

EXAMPLE 6

A suspension of 50.0 g of crude dicalcium 2-keto-D-glucarate [the content as dicalcium 2-keto-D-glucarate trihydrate (C$_6$H$_6$O$_8$Ca.3H$_2$O) as determined by high performance liquid chromatography being 85.1%; 0.1417 mole] in 800 ml of acetone was stirred at room temperature while 17.19 g (0.17 mole) of 97% sulfuric acid was added dropwise slowly. After completion of the addition, the mixture was stirred for further 10 hours. The insoluble matter was filtered off and washed with about 300 ml of acetone. The filtrate and the washings were combined and concentrated to dryness under reduced pressure, 100 ml of concentrated hydrochloric acid was added to the residue and the mixture was heated at 70° C. for 20 minutes. The reaction mixture was concentrated to dryness under reduced pressure 100 ml of water and 0.5 g of active carbon were added to the residue and the mixture was heated at 70° C. for about 5 minutes. The active carbon was removed by filtration, and the filtrate was concentrated to dryness under reduced pressure. Ether-acetonitrile was added to the residue, and the insoluble matter was collected by filtration, washed with a small amount of dichloromethane and then dried in a desiccator under reduce pressure to give 22.2 g of D-glucosaccharoascorbic acid.-monohydrate (Purity 98.8%) (Yield 74.4%) Melting point: 188°–189° C. (decomposition) (recrystallized from acetone-benzene).

EXAMPLE 7

A mixture composed of 5 millimoles of a 2-keto-D-glucaric acid 2,3-O-ketal or acetal salt or 5 millimoles (in total) of a mixture of these and 10 ml of 15% hydrochloric acid was stirred at 65° C. for 1 hour. Thereafter, the whole amount was made 50 ml and assayed by high performance liquid chromatography in the same manner as in Example 2. D-Glucosaccharoascorbic acid was formed in the yield shown in Table 2.

TABLE 2

| No. | Starting material (molecular formula) | D-Glucosaccharoascorbic acid Yield (%) |
|---|---|---|
| 1 | Disodium 2,3-O-isopropylidene-2-keto-D-glucarate (C$_9$H$_{10}$O$_8$Na$_2$.2H$_2$O) 1641 mg | 88.7 |
| 2 | Dicalcium 2,3-O-isopropylidene-2-keto-D-glucarate (C$_9$H$_{10}$O$_8$Ca.2H$_2$O) 1611 mg | 80.1 |
| 3 | Dibarium 2,3-O-isopropylidene- | 83.2 |

TABLE 2-continued

| No. | Starting material (molecular formula) | D-Glucosaccharoascorbic acid Yield (%) |
|---|---|---|
|  | 2-keto-D-glucarate ($C_9H_{10}O_8Ba \cdot 2H_2O$) 2098 mg |  |
| 4 | Dicalcium 2-keto-D-glucarate ($C_6H_6O_8Ca \cdot 3H_2O$) 1501 mg | 84.2 |
| 5 | Monosodium 2-keto-D-glucarate ($C_6H_7O_8Na \cdot H_2O$) 1241 mg | 88.3 |
| 6 | Dicalcium 2,3-O-isopropylidene-2-keto-D-glucarate ($C_9H_{10}O_8Ca \cdot 2H_2O$) 805 mg Dicalcium 2-keto-D-glucarate ($C_6H_6O_8Ca \cdot 3H_2O$) 750 mg | 82.5 |

EXAMPLE 8

500 g of crude dicalcium 2-keto-D-glucarate [the content of dicalcium 2-keto-D-glucarate trihydrate ($C_6H_6O_8Ca \cdot 3H_2O$) being 85.1%; 1.417 moles] was suspended in 1500 ml of distilled water, and to the suspension was gradually added 214.9 g of 97% sulfuric acid (2.1255 moles) under agitation at room temperature. After the addition, the mixture was further stirred overnight at room temperature. The insoluble matter was collected by filtration and washed with 1000 ml of distilled water. The wash water was mixed with the filtrate. Thus obtained filtrate was concentrated under reduced pressure on a bath at 55° C. until the concentrate amounted to 300 ml. After cooling, the insoluble matter was filtered off. The filtrate was warmed for 8 hours on a water bath at 55° C., and concentrated under reduced pressure. To the concentrate was added 200 ml of distilled water and the insoluble matter was filtered off. Thus obtained solution was passed through the column which had packed with 300 ml of active carbon (Shirasagi ®; special grade for chromatography; manufactured and sold by Takeda Chemical Co., Ltd.) with the aid of water. The elution was carried out by using distilled water. The eluate was concentrated under reduced pressure, and the precipitated crystals were collected by filtration, and dried to give the first crude crystals. The filtrate was passed through the column packed with active carbon. The eluate was concentrated under reduced pressure, and the precipitated crystals were collected by filtration, and dried to give the second crude crystals. The filtration was further treated in the same manner as above to give the third crude crystals. The third crude crystals were mixed with the first and the second crystals sufficiently. There were obtained 247 g of crude D-glucosaccharoascorbic acid-monohydrate. Purity 96.8%, Yield 81.1%.

Pure D-glucosaccharoascorbic acid.monohydrate was obtained by recrystallization of the crude D-glucosaccharoascorbic acid.monohydrate from distilled water.

Melting point 134°–138° C.

Elemental analysis (%) For $C_6H_8O_8$ Calculated: C, 34.63; H, 3.87 Found: C, 34.52; H, 3.89.

IR (KBr), cm$^{-1}$: 3580, 3500, 3400–3000, 1770, 1720, 1690, 1590.

As a procedure for removing water of crystallization from D-glucosaccharoascorbic acid.monohydrate, there may be mentioned recrystallization from anhydrous organic solvent and dryness under reduced pressure. Azeotropic dehydration is alternatively adaptable as described below.

To 10 g of D-glucosaccharoascorbic acid.monohydrate was added 100 ml of acetonitrile. The distillation of the acetonitrile was continued under ordinary pressure using a distillation apparatus, while the acetonitrile equal to the amount of the distilled acetonitrile was continuously incorporated into the apparatus. 250 ml of acetonitrile was distilled off in total. With the distillation of acetonitrile, anhydrous D-glucosaccharoascorbic acid began to precipitate. After the distillation, the precipitates were collected by filtration and dried to give 8.8 g of D-glucosaccharoascorbic acid. (Yield 96.3%) This product was completely identical with the m.p., IR, $^1$H-NMR, 13C-NMR and retention time of high performance liquid chromatography.

EXAMPLE 9

A solution of 1.0 g (5.26 millimoles) of D-glucosaccharoascorbic acid in 10 ml of distilled water was applied to a column packed with 30 ml of Dowex 50W-X8 (cation exchange resin of Dow Chemical, U.S.A.) (Na$^+$ form). Elution was carried out with distilled water to give an eluate (400 ml). This eluate was concentrated under reduced pressure, 10 ml of methanol was added to the residue, and the mixture was stirred overnight. The precipitate was collected by filtration and dried in a desiccator under reduced pressure to give 0.57 g of monosodium D-glucosaccharoascorbate. (Yield 45.3%)

Melting point: about 170° C. (decomposition).

Elemental analysis (%): For $C_6H_5O_7Na \cdot 1.5H_2O$ Calculated: C, 30.14; H, 3.37. Found: C, 30.38; H, 3.21.

IR (KBr), cm$^{-1}$: 3600–2800, 1750, 1680, 1620, 1420

EXAMPLE 10

D-Glucosaccharoascorbic acid (1.90 g, 0.01 mole) was added to 30 ml of distilled water and the mixture was stirred at room temperature. To the resultant aqueous solution was added 1.06 g (0.01 mole) of sodium carbonate, and the mixture was stirred until carbon dioxide gas generation ceased. The reaction mixture obtained was added dropwise to 300 ml of methanol. The resultant precipitate was collected by filtration and dried under reduced pressure to give 2.50 g of disodium D-glucosaccharoascorbate. (Yield 99.2%)

Melting point: 185° C. (decomposition).

Elemental analysis (%): For $C_6H_4O_7Na \cdot H_2O$ Calculated: C, 28.59; H, 2.40. Found: C, 28.67; H, 2.61.

EXAMPLE 11

A solution of 1.0 g (5.26 millimoles) of D-glucosaccharoascorbic acid in 10 ml of distilled water was applied to a column packed with 100 ml of IR-120B (cation exchange resin of Rohm and Haas, USA) (K$^+$ form). Elution was carried out with distilled water to give an eluate (400 ml, pH 5.17). This eluate was concentrated under reduced pressure, 400 ml of methanol was added to the residue, and the resultant precipitate was collected by filtration and dried in a desiccator under reduced pressure to give 1.12 g of monopotassium D-glucosaccharoascorbate. (Yield 83.5%)

Melting point: about 250° C. (decomposition).

Elemental analysis (%): For $C_6H_5O_7K \cdot 1.5H_2O$ Calculated: C, 28.24; H, 3.16. Found: C, 28.10; H, 2.83.

IR (KBr), cm$^{-1}$: 3600–2800, 1760, 1660, 1600.

EXAMPLE 12

D-Glucosaccharoascorbic acid (1.90 g, 0.01 mole) was added to 30 ml of distilled water and the mixture was stirred at room temperature. To the resultant aqueous solution was added 1.38 g (0.01 mole) of potassium carbonate, and the mixture was stirred until carbon dioxide gas generation ceased. The reaction mixture obtained was added dropwise to 300 ml of methanol. The precipitate was collected by filtration and dried under reduced pressure to give 2.70 g of dipotassium D-glucosaccharoascorbate. (Yield 95.0%)

Melting point: 175° C. (decomposition)

Elemental analysis (%): For $C_6H_4O_7K_2 \cdot H_2O$ Calculated: C, 25.35; H, 2.13. Found: C, 25.23; H, 2.31.

IR (KBr), cm$^{-1}$: 3600–2900, 1720, 1590, 1400

EXAMPLE 13

A solution of 1.0 g (5.26 millimoles) of D-glucosaccharoascorbic acid in 10 ml of distilled water was applied to a column packed with 30 ml of Dowex 50W-X8 (cation exchange resin of Dow Chemical, U.S.A.) ($Ca^{++}$ form). Elution was carried out with distilled water to give an eluate (400 ml, pH 3.5). This eluate was concentrated under reduced pressure, 20 ml of acetone was added to the residue, and the resultant precipitate was collected by filtration and dried in a desiccator under reduced pressure to give 0.96 g of monocalcium D-glucosaccharoascorbate. (Yield 81.6%)

Melting point: 190°–205° C. (decomposition).

Elemental analysis (%): For $C_6H_5O_7\frac{1}{2}Ca \cdot 0.8H_2O$ Calculated: C, 32.27; H, 2.98 Found: C, 32.13; H, 3.19.

IR (KBr), cm$^{-1}$: 3600–2800, 1760, 1680, 1600

EXAMPLE 14

D-Glucosaccharoascorbic acid (1.90 g, 0.01 mole) was added to 30 ml of distilled water and the mixture was stirred at room temperature. To the resultant aqueous solution was added 0.741 g (0.01 mole) of calcium hydroxide and, after 30 minutes, the resultant precipitate was collected by filtration and dried under reduced pressure to give 2.2 g of dicalcium D-glucosaccharoascorbate. (Yield 78.0%)

Melting point: 175° C. (decomposition).

Elemental analysis (%): For $C_6H_4O_7Ca \cdot 3H_2O$ Calculated: C, 25.54; H, 3.57.
Found: C, 25.23; H, 3.84.

EXAMPLE 15

Quality Improving Agent 1

In ethanol was dissolved 0.4 g of D-glucosaccharoascorbic acid to make the whole volume 50 ml to prepare Quality Improving Agent 1 for oils and fats or food products containing oils and fats.

Figure 1:
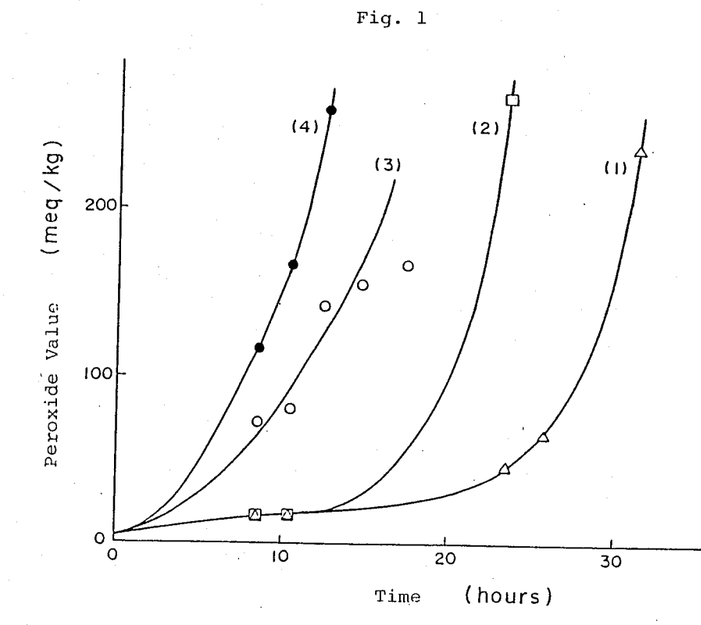

To 20 ml each of soybean oil [peroxide value (hereinafter abbreviated as POV): 2,85 meg/kg]was respectively added 0.5 ml of Quality Improving Agent 1, and of each ethanol solution of L-ascorbic acid and BHT (Dibutyl hydroxy toluene) to thereby prepare samples of soybean oil as shown in Table 3. These samples were subjected to oxidation by means of a testing device of stability of fats and oils (AOM Determination Device, manufactured by Kuramochi Kagaku Kikai Seisakusho, Ltd.) at 97.8±1° C. with aeration of 2.33 ml/sec., and the respective POV's were determined with passage of time, the results being shown on FIG. 1. The FIG. 1 is a curve showing change of the peroxide value of soybean oil containing various additives.

TABLE 3

| Exp. No. | Additive | Amount W/V% |
| --- | --- | --- |
| (1) | D-glucosaccharoascorbic acid | 0.02 |
| (2) | L-ascorbic acid | 0.02 |
| (3) | BHT | 0.02 |

TABLE 3-continued

| Exp. No. | Additive | Amount W/V% |
| --- | --- | --- |
| (4) | None | — |

In general, the stability of oils and fats is expressed in terms of the time in the course of which the POV of a sample oil becomes constant, and the longer the time is more stable the sample. As shown in FIG. 1, until the respective POV's reached 100 meg/kg, L-ascorbic acid (Experiment No. (2)) required 20 hours, and BHT (Experiment No. (3)) did 11 hours, while the agent of this invention (Experiment No. (1)) did 28 hours. Thus, the agent of this invention is far excellent in antioxidant effect as compared with conventional antioxidants.

EXAMPLE 16

Quality Improving Agent 2

In ethanol were dissolved 0.4 g of D-glucosaccharoascorbic acid and 0.4 g of natural tocopherol to make the whole volume 50 ml to prepare Quality Improving Agent 2 for oils and fats or food products containing oils and fats. To 20 ml each of linoleic acid (POV : 0.5 meg/kg) was respectively added 0.5 ml of Quality Improving Agent 2, and of each ethanolic solution of BHT and natural tocopherol to thereby prepare samples of linoleic acid as shown in Table 4. These samples were subjected to oxidation by means of the same testing device and under the same conditions as in Example 15, and the respective POV's were determined with passage of time, the results being shown on FIG. 2. The FIG. 2 is a curve showing change of the peroxide value of linoleic acid containing various additives

TABLE 4

| Exp. No. | Additive | Amount W/V% |
| --- | --- | --- |
| (1) | D-glucosaccharoascorbic acid | 0.02 |
|  | Natural tocopherol | 0.02 |
| (2) | BHT | 0.02 |
| (3) | Natural tocopherol | 0.02 |
| (4) | None | — |

Figure 2:
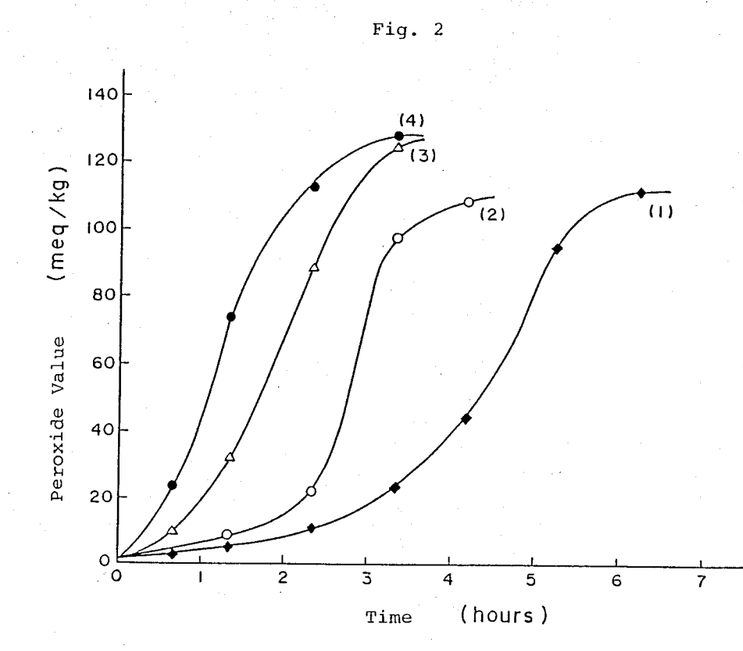

As shown in FIG. 2, until the respective POV's reached 100 meq/kg, BHT (Experiment No.(2)) required 3.5 hours and natural tocopherol (Experiment No.(3)) did 2.5 hours, while the agent of this invention (Experiment No. (1)) did 5.4 hours. Thus, the agent of this invention is far excellent in antioxidant effect as compared with conventional antioxidants.

EXAMPLE 17

Figure 3:
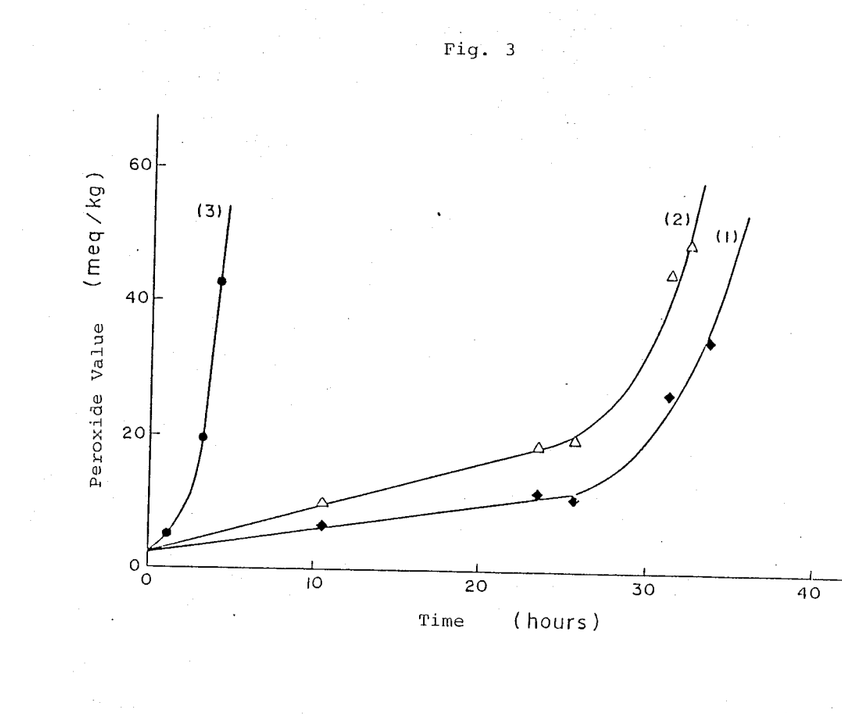

To 20 ml each of lard (POV: 2.5 meq/kg) was respectively added 0.5 ml of Quality Improving Agent 2 prepared in Example 16 and of ethanolic solution of natural tocopherol to thereby prepare samples of lard as shown in Table 5. These samples were subjected to oxidation by means of the same device and under the same conditions as in Example 15, then the respective POV's were determined with passage of time, the results being shown on FIG. 3. The FIG. 3 is a curve showing change of the peroxide value of lard containing various additives.

TABLE 5

| Exp. No. | Additive | Amount W/V% |
| --- | --- | --- |
| (1) | D-glucosaccharoascorbic acid | 0.02 |
|  | Natural tocopherol | 0.02 |
| (2) | Natural tocopherol | 0.02 |

TABLE 5-continued

| Exp. No. | Additive | Amount W/V% |
|---|---|---|
| (3) | None | — |

As shown on FIG. 3, until the respective POV's reached 20 meq/kg, natural tocopherol (Experiment No.(2)) required 25 hours, while Quality Improving Agent 2 did 30 hours showing excellent antioxidant effect.

EXAMPLE 18

Lean portion of tuna was cut into a size of 1.5 cm×1.5 cm×6 cm, which was immersed in a 1.0% aqueous solution of disodium D-glucosaccharoascorbate for two minutes then stored in a refrigerator at 5°–8° C. for 21 hours, and the change of its color was observed with the naked eye. As the controls, non-treated lean portion of tuna and another lean portion of tuna immersed in a 1.0% aqueous solution of sodium L-ascorbate were provided. The results are shown in Table 6.

TABLE 6

| Additive | Discoloration after 21 hrs. |
|---|---|
| Present invention | |
| Disodium D-glucosac-charoascorbate | No change |
| Control | |
| None | About half of the lean portion was blackened |
| Sodium L-ascorbate | About one-fourth of the lean portion was blackened |

EXAMPLE 19

Figure 4:
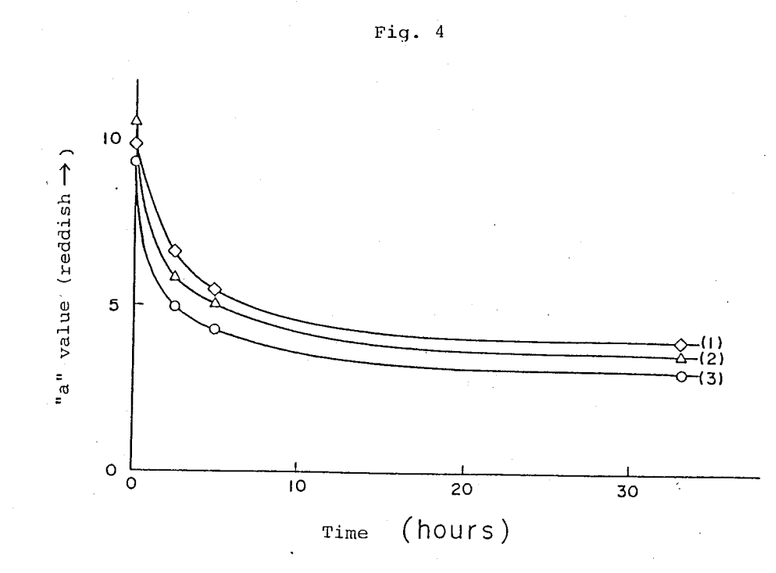

Samples of pork sausage were prepared by adding, in the course of manufacture, table salt and sodium sulfite and sodium polyphosphate and two different amounts of disodium D-glucosaccharoascorbate as shown in Table 7 (In addition to this as a control was provided a sample containing no antioxidant). Thus manufactured samples including the control were stored in a refrigerator for 20 hours at 5°–8° C. These samples were cut into a size of 15 mm thick, put in polyethylene bags, which were stored at room temperature (under irradiation of fluorescent lamp), and the change of color was observed by using a color-difference meter, the results being expressed in terms of "a" value in accordance with Hunter's method. The larger the "a" value is, the greater degree of redness is shown. The change of "a" value with passage of time is shown on FIG. 4. The FIG. 4 is a curve showing change of the degree ("a" value) of reddish tinge of pork sausage. The hour shown by the axis of this graph means the lapsed time after the sausage were cut into 15 mm thick. As seen on FIG. 4, the samples of the sausage to which the agent of this invention is stronger in color development and less in discoloration as compared with the control.

TABLE 7

Minced pork lean meat
400 g

Packing into casing (vinylidene chloride tube of 30 mm dia.)

↓

Heating (80° C. for 40 minutes)

↓

Cooling (in running water)

EXAMPLE 20

Quality Improving Agent 3

To 10 g of D-glucosaccharoascorbic acid and 10 g of table salt was added water to make the whole volume 1000 ml, and Quality Improving Agent 3 for fruits was prepared.

To glass containers was added 1000 ml each portion of 1% aqueous solution of D-glucosaccharoascorbic acid and Quality Improving Agent 3, in which was immersed sliced peach, then the containers were closed tightly. The color changes of the liquid portion and the sliced peach were observed with naked eyes. On the other hand, in each of water, a 1% aqueous solution of table salt, a 1% aqueous solution of L-ascorbic acid and an aqueous solution containing 1% of L-ascorbic acid and 1% of table salt was immersed sliced peach. The containers were tightly closed and used as the control. From the results shown in Table 8, it was observed that the agent of this invention was effective in preventing browning of peach and that, in the liquid containing the agent of this invention, appearance of cloud was prevented.

TABLE 8

| Solution in which samples were immersed | Elapse of time | | | |
|---|---|---|---|---|
| | 2 hours | 5 hours | 3 days | 5 days |
| 1% aqueous solution of D-glucosaccharoascorbic acid | ⊙ | ⊙ | ⊙* | ○* |
| Quality Improving Agent 3 | ⊙ | ⊙ | ⊙* | ⊙* |
| Water | Δ | Δ | x** | x** |
| 1% aqueous saline solution | ⊙ | Δ | x** | x** |
| 1% aqueous solution of L-ascorbic solution | ⊙ | ⊙ | ○** | ○** |
| Aqueous solution containing 1% of L-ascorbic acid and 1% of table salt | ⊙ | ⊙ | ○* | ○** |

Note
⊙ No discoloration
○ Slightly discolored
Δ Browning
x Remarkably browning
*Clear impression
**Cloud appeared

We claim:
1. A compound selected from the group consisting of D-glucosaccharoascorbic acid of the formula

2. A compound according to claim 1, wherein the D-glucosaccharoascorbic acid and the salt are in the form of hydrate, respectively.

3. A compound according to claim 1, wherein the salt is an alkali metal salt or an alkaline earth metal salt.

4. A compound according to claim 1, wherein the alkali metal salt and the alkaline earth metal salt are a mono- or di-salt.

* * * * *

UNITED STATES PATENT AND TRADEMARK OFFICE
CERTIFICATE OF CORRECTION

PATENT NO. : 4,959,483
DATED : September 25, 1990
INVENTOR(S) : Koichi MATSUMURA It is certified that error appears in the above-identified patent and that said Letters Patent is hereby corrected as shown below:

On the title page, under item [19], "Matsumura et al." should be --Matsumura--.

On the title page, item [75], delete "; Hiroshi Kimura, Suita; Noritoshi Mise, Takatsuki; Hiroshi Miki, Suita, all of", leaving only Koichi Matsumura, Ibaraki, Japan as the sole inventor.

Signed and Sealed this

Twenty-first Day of April, 1992

Attest:

HARRY F. MANBECK, JR.

*Attesting Officer*  *Commissioner of Patents and Trademarks*